United States Patent
Marshall et al.

(10) Patent No.: US 11,241,289 B2
(45) Date of Patent: Feb. 8, 2022

(54) PACKAGING INSERT

(71) Applicant: CMR Surgical Limited, Cambridge (GB)

(72) Inventors: Keith Marshall, Cambridge (GB); Nikki Priyam Su-Ling Phoolchund, Cambridge (GB); Thomas Bates Jackson, Cambridge (GB)

(73) Assignee: CMR SURGICAL LIMITED, Cambridge (GB)

(*) Notice: Subject to any disclaimer, the term of this patent is extended or adjusted under 35 U.S.C. 154(b) by 228 days.

(21) Appl. No.: 16/333,067

(22) PCT Filed: Sep. 13, 2017

(86) PCT No.: PCT/GB2017/052696
§ 371 (c)(1),
(2) Date: Mar. 13, 2019

(87) PCT Pub. No.: WO2018/051082
PCT Pub. Date: Mar. 22, 2018

(65) Prior Publication Data
US 2019/0223965 A1 Jul. 25, 2019

(30) Foreign Application Priority Data
Sep. 14, 2016 (GB) .................................... 1615615

(51) Int. Cl.
A61B 34/30 (2016.01)
A61B 50/30 (2016.01)
(Continued)

(52) U.S. Cl.
CPC .............. A61B 34/30 (2016.02); A61B 46/10 (2016.02); A61B 50/00 (2016.02); A61B 50/30 (2016.02);
(Continued)

(58) Field of Classification Search
CPC ......... A61B 34/30; A61B 50/00; A61B 50/30; A61B 46/10; A61B 2017/00477;
(Continued)

(56) References Cited

U.S. PATENT DOCUMENTS

2003/0168370 A1* 9/2003 Merboth .................. A01N 1/02
206/438
2006/0161138 A1 7/2006 Orban, III et al.
(Continued)

FOREIGN PATENT DOCUMENTS

EP 2792308 A2 10/2014
GB 1399884 A 7/1975
(Continued)

OTHER PUBLICATIONS

V. Ekstrand, International Search Report issued in application No. PCT/GB2017/052696 completion date Nov. 9, 2017, dated Nov. 20, 2017, 4 pages.
(Continued)

Primary Examiner — Kathleen S Holwerda
Assistant Examiner — Uyen N Vo
(74) Attorney, Agent, or Firm — King & Spalding LLP

(57) ABSTRACT

A packaging insert configured to engage a portion of a surgical drape for locating the drape on a surgical robot arm, the drape comprising a drive transfer element for transferring drive between the robot arm and a surgical instrument, the packaging insert comprising a body and a retention portion engageable with the drive transfer element for retaining the drive transfer element in a desired position.

19 Claims, 9 Drawing Sheets

(51) Int. Cl.
  *A61B 46/10* (2016.01)
  *A61B 50/00* (2016.01)
  *A61B 17/00* (2006.01)

(52) U.S. Cl.
  CPC .............. *A61B 2017/00477* (2013.01); *A61B 2034/302* (2016.02)

(58) Field of Classification Search
  CPC .. A61B 2034/302; B65D 73/00; B65D 81/00; B65D 85/00; A61F 2/0095; A61F 2002/2835; B65B 25/00; B65B 2220/16; A01N 1/0263; A01N 1/02
  See application file for complete search history.

(56) References Cited

U.S. PATENT DOCUMENTS

| | | | | |
|---|---|---|---|---|
| 2008/0140088 | A1* | 6/2008 | Orban, III | A61B 34/30 606/130 |
| 2010/0175019 | A1 | 7/2010 | Sitton et al. | |
| 2014/0180272 | A1 | 6/2014 | Dachs, II et al. | |
| 2014/0261456 | A1* | 9/2014 | Malackowski | A61B 34/20 128/849 |
| 2015/0202009 | A1* | 7/2015 | Nussbaumer | A61B 46/27 128/856 |
| 2016/0135895 | A1* | 5/2016 | Faasse | B65D 81/24 206/204 |
| 2016/0242861 | A1* | 8/2016 | Flatt | A61B 46/10 |

FOREIGN PATENT DOCUMENTS

| | | |
|---|---|---|
| GB | 2329127 A | 3/1999 |
| GB | 2538230 A | 11/2016 |
| JP | 2007-167644 A | 7/2007 |
| JP | 3191388 U | 6/2019 |
| WO | WO 2007/041093 A1 | 4/2007 |
| WO | WO 2016/064758 A1 | 4/2016 |
| WO | WO 2016/081286 A1 | 5/2016 |
| WO | WO 2016/090459 A1 | 6/2016 |

OTHER PUBLICATIONS

International Search Report issued for International Patent Application No. GB1615615.0 dated Feb. 17, 2017, 3 pages.
Notice of Refusal issued in Japanese Application No. 2019-535989, dated Jul. 20, 2021, 4 pages.

* cited by examiner

PACKAGING INSERT

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between the base 201 and an articulation 203. The articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

A surgeon utilises many instruments during the course of a typical laparoscopy operation. For this reason, it is desirable for the instruments to be detachable from and attachable to the end of the robot arm with an ease and speed which enables instruments to be exchanged mid-operation. It is therefore desirable to minimise the time taken and maximise the ease with which one instrument is detached from a robot arm and a different instrument is attached.

The operating theatre is a sterile environment. Surgical instruments are sterilised prior to use in an operation. It is desirable that the robot arm is shrouded with a sterile drape so as to avoid the need to sterilise it prior to use. Existing sterile drapes can be cumbersome to use and can take a long time to apply over the robot arm. There is a need for an improved mechanism for applying a sterile drape over a robot arm.

SUMMARY

According to an aspect of the present invention, there is provided a packaging insert configured to engage a portion of a surgical drape for locating the drape on a surgical robot arm, the drape comprising a drive transfer element for transferring drive between the robot arm and a surgical instrument, the packaging insert comprising a body; and a retention portion engageable with the drive transfer element for retaining the drive transfer element in a desired position.

Suitably the packaging insert comprises an engagement portion releasably engageable with the drape. Suitably the retention portion comprises at least one of a recess, an aperture and a protruding portion.

Suitably the retention portion comprises an aperture in the body, the aperture comprising a first edge, and the first edge being configured to retain the drive transfer element in the desired position. Suitably the aperture comprises a second edge opposing the first edge, the first edge and the second edge being spaced apart so as to be frictionally engageable with opposing sides of the drive transfer element.

Suitably the drape comprises three drive transfer elements, and the packaging insert comprises three apertures in the body, each aperture being configured to receive a respective one of the drive transfer elements therethrough and comprising a respective edge configured to retain the respective drive transfer element in the desired position.

Suitably the packaging insert comprises a handle.

Suitably the engagement portion is provided on an underside of the body. Suitably the engagement portion comprises a lip engageable with a drape lip provided on the drape. Suitably the engagement portion comprises a plurality of lips for engagement with a respective one of a plurality of drape lips provided on the drape.

Suitably the packaging insert comprises a deformable portion configured to deform so as to move at least one lip from a position in which the lip is engaged with a respective drape lip to a position in which the lip is disengaged from the respective drape lip. Suitably the packaging insert comprises a deformable portion corresponding to each lip, the deformable portion being configured to deform so as to move the respective lip from a position in which the lip is engaged with a respective drape lip to a position in which the lip is disengaged from the respective drape lip.

Suitably the engagement portion comprises an adhesive portion which is releasably adherable to the drape.

Suitably the packaging insert comprises a side portion, the engagement portion being provided on the side portion. Suitably the packaging insert comprises two side portions, one to either side of the body, the packaging insert comprising two engagement portions, one engagement portion being provided on each of the side portions.

Suitably the engagement portion comprises a protrusion configured to protrude into a corresponding recess on the drape, the protrusion being sized to engage with the recess in an interference fit so as to frictionally engage therewith.

Suitably the engagement portion is configured to engage with the drape with a weaker engagement than an engagement between the drape and the robot arm such that the drape is preferentially retained on the robot arm.

Suitably the packaging insert is formed from a single piece of material by at least one of stamping and bending. Suitably the packaging insert comprises a rigid and/or a semi-rigid material.

Suitably the packaging insert is configured to be packaged together with the drape.

According to another aspect of the present invention, there is provided a surgical drape assembly comprising a drape for covering a surgical robot and a packaging insert as described above. Suitably the drape comprises reinforcement portions.

Any one or more feature of any aspect above may be combined with any one or more feature of that aspect and/or any other aspect above. Any apparatus feature may be written as a method feature where possible, and vice versa. These have not been written out in full here merely for the sake of brevity.

This Summary is provided to introduce a selection of concepts in a simplified form that are further described below in the Detailed Description. The mention of features in this Summary does not indicate that they are key features or essential features of the invention or of the claimed subject matter, nor is it to be taken as limiting the scope of the claimed subject matter.

BRIEF DESCRIPTION OF THE FIGURES

The present invention will now be described by way of example with reference to the accompanying drawings. In the drawings:

FIG. 7b illustrates the other side of the interface structure of FIG. 7a;

FIG. 10b illustrates a schematic side view of the packaging insert of FIG. 10a;

FIG. 11b illustrates a schematic partial side view of the packaging insert of FIG. 11a;

DETAILED DESCRIPTION

Figure 3:
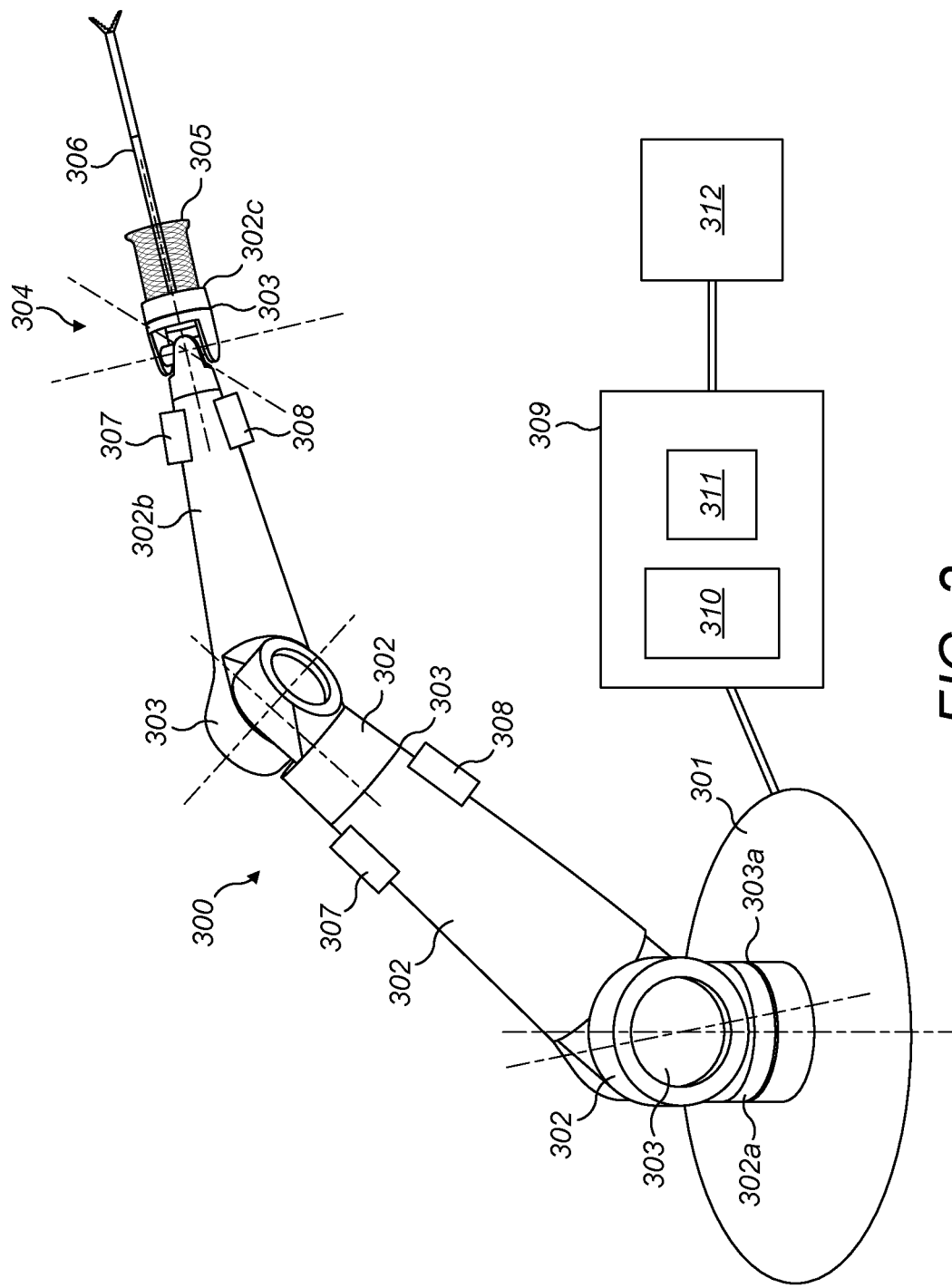
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by a proximal joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our patent application PCT/GB2014/053523.

Figure 1:
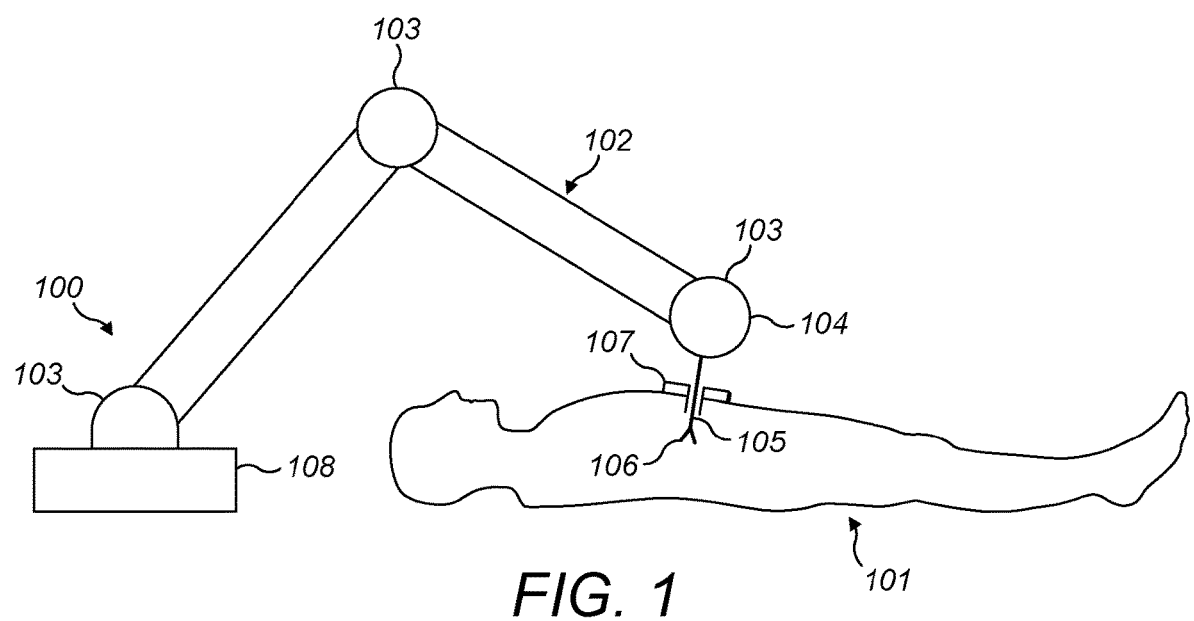
FIG. 1 illustrates a surgical robot performing a surgical procedure.
Figure 2:
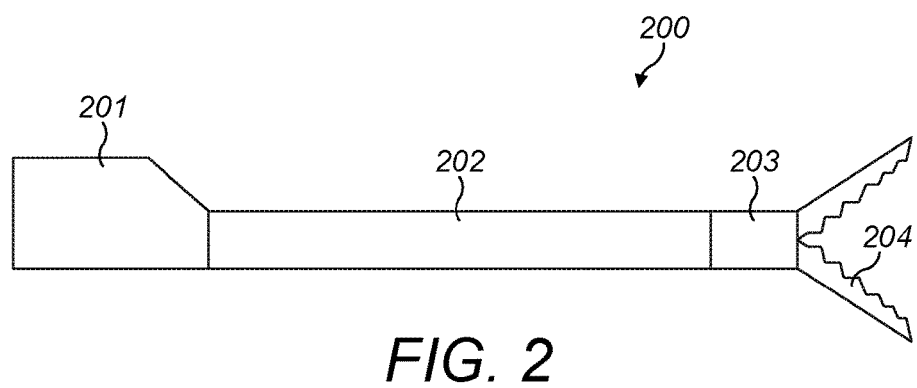
FIG. 2 illustrates a known surgical instrument.

The arm terminates in the attachment 305 for interfacing with the instrument 306. Suitably, the instrument 306 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable to and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed within the robot arm. The controllers are connected via a communication bus to a control unit 309. The control unit 309 comprises a processor 310 and a memory 311. The memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in the memory 311 is configured to respond to those inputs and cause the joints of the arm and instrument to move accordingly, in compliance with a predetermined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
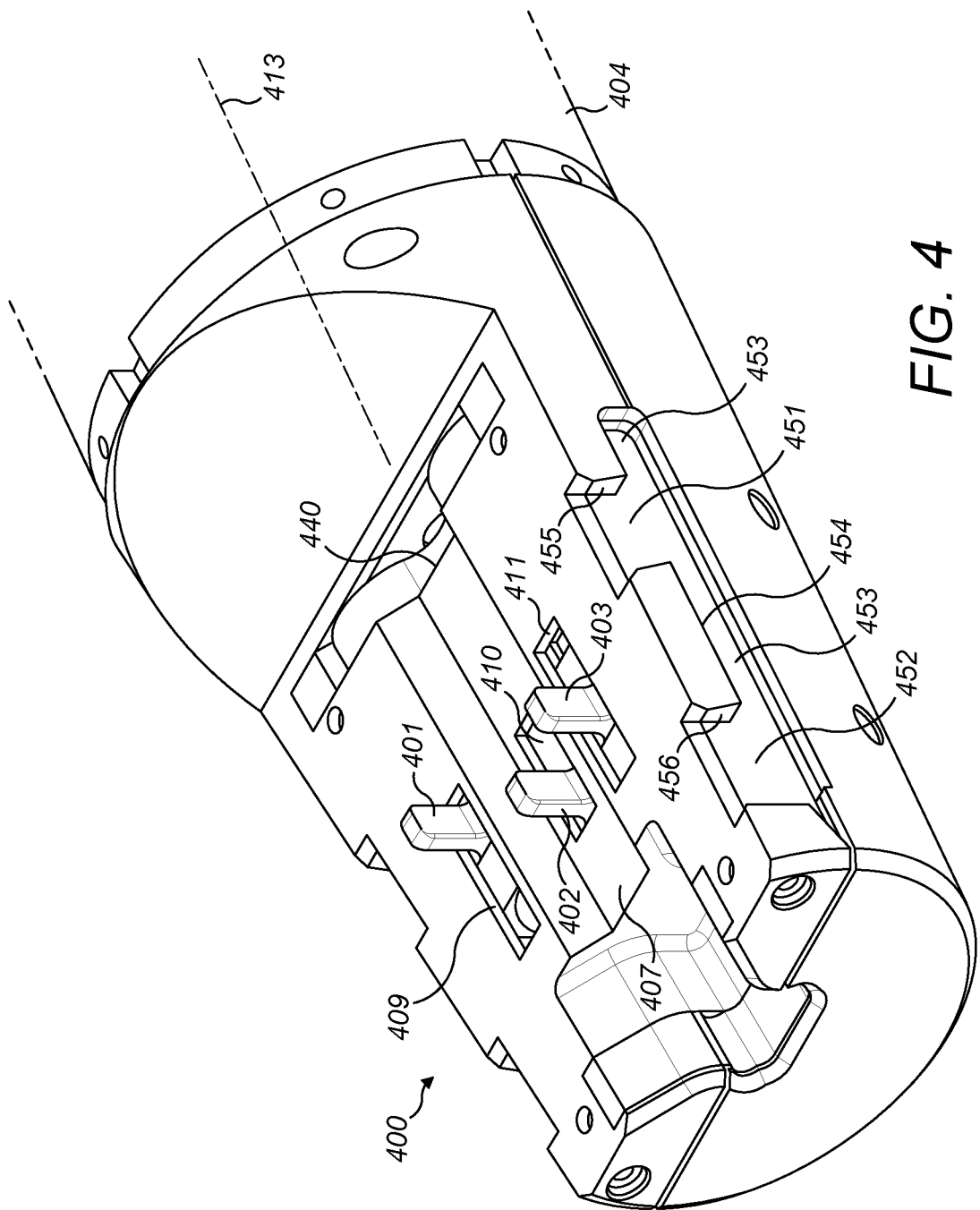
FIG. 4 illustrates a drive assembly interface of a surgical robot arm.
Figure 5:
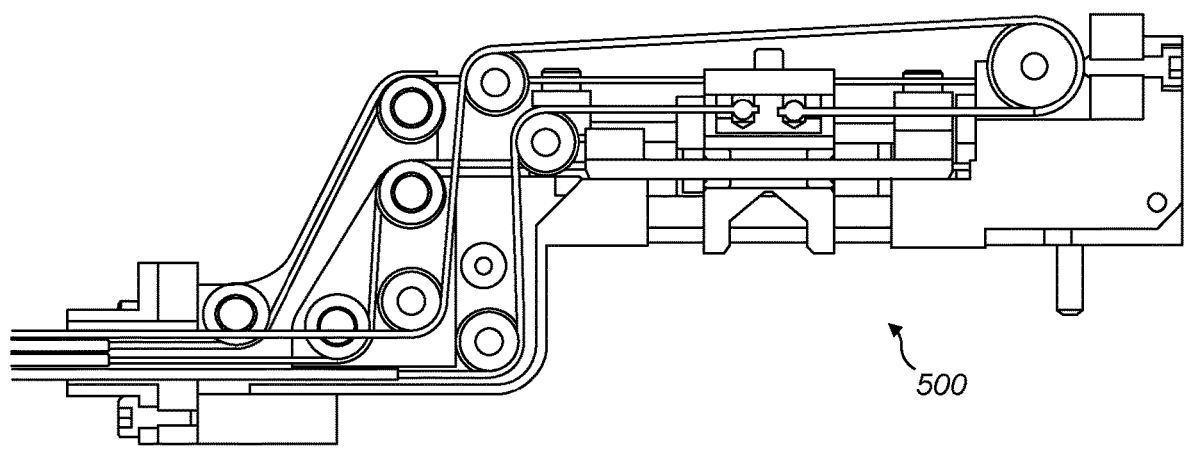
FIG. 5 illustrates an instrument interface of a surgical instrument.
Figure 6:
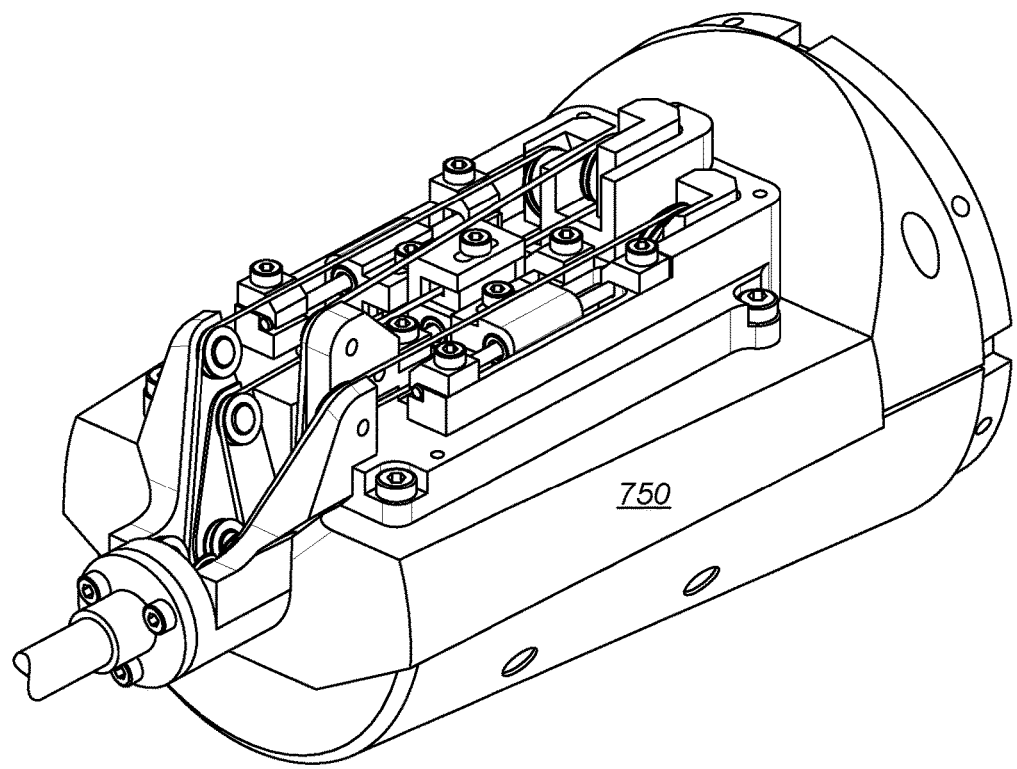
FIG. 6 illustrates the drive assembly interface of a robot arm with attached instrument.

FIGS. 4 and 5 illustrate an exemplary mechanical interconnection of the drive assembly interface and the instrument interface in order to transfer drive from the robot arm to the instrument. FIG. 6 illustrates the instrument mounted to the drive assembly. FIG. 4 illustrates an exemplary drive assembly interface 400 at the end of a robot arm 404. The drive assembly interface 400 comprises a plurality of drive assembly interface elements 401, 402, 403. FIG. 4 illustrates three drive assembly interface elements. In other examples, there may be greater than or fewer than three drive assembly interface elements. The drive assembly interface elements 401, 402, 403 are movable within the drive assembly interface 400 along linear paths 409, 410, 411. In the illustrated example, the linear paths 409, 410, 411 are disposed on two parallel planes. The central linear path 410 is disposed on a plane 407 set into the drive assembly interface 400 compared to that in which the outer two linear paths 409, 411 are disposed. In other implementations, the three linear paths 409, 410, 411 can be disposed on the same plane, or all on different planes.

During an operation or surgical procedure, the surgical robot is shrouded in a sterile drape to provide a sterile barrier between the non-sterile surgical robot and the sterile operating environment. The surgical instrument is sterilised before being attached to the surgical robot. The sterile drape is typically constructed of a plastic sheet, for example made of polyester, polypropylene, polyethylene or polytetrafluoroethylene (PTFE). Suitably, the drape is flexible and/or deformable. It is desirable for the sterile drape to be easily and quickly placed in position over the robot arm. It is also desirable for the drape to be easily engageable with the robot arm to effectively interface with the robot arm. This can help reduce time taken in preparing the robot arm for surgery. Using such a drape on the robot arm can mean that the patient is not exposed to the non-sterile surgical robot arm. When exchanging instruments mid-operation, it is desirable for the sterile barrier to be maintained.

Figure 7A:
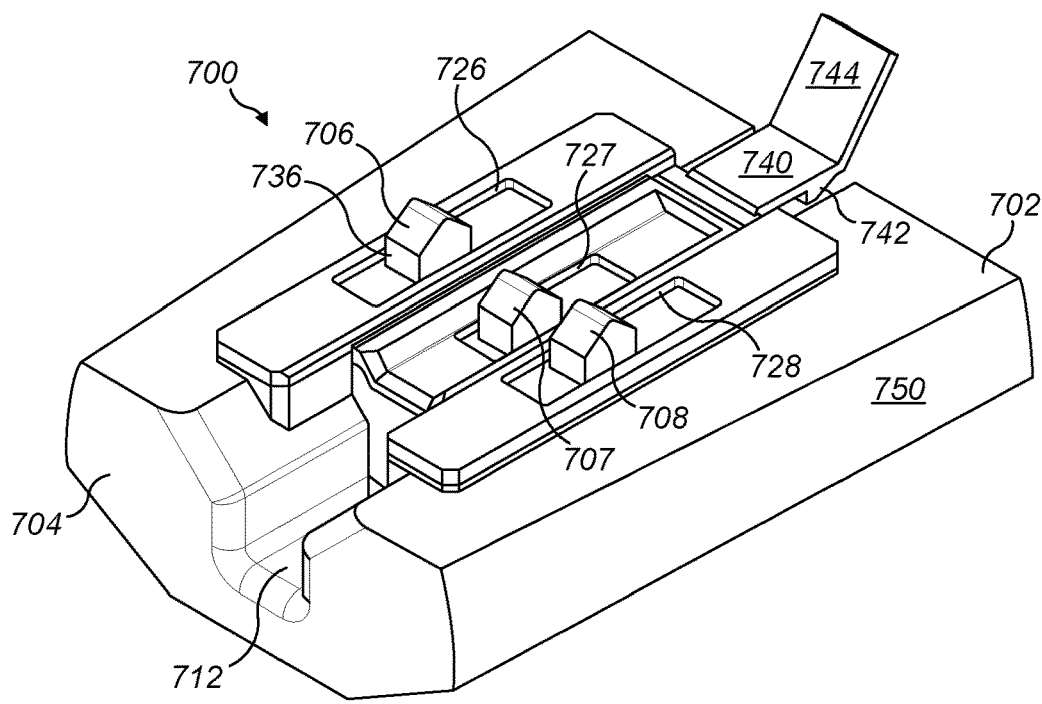
FIG. 7a illustrates one side of an interface structure.
Figure 7B:
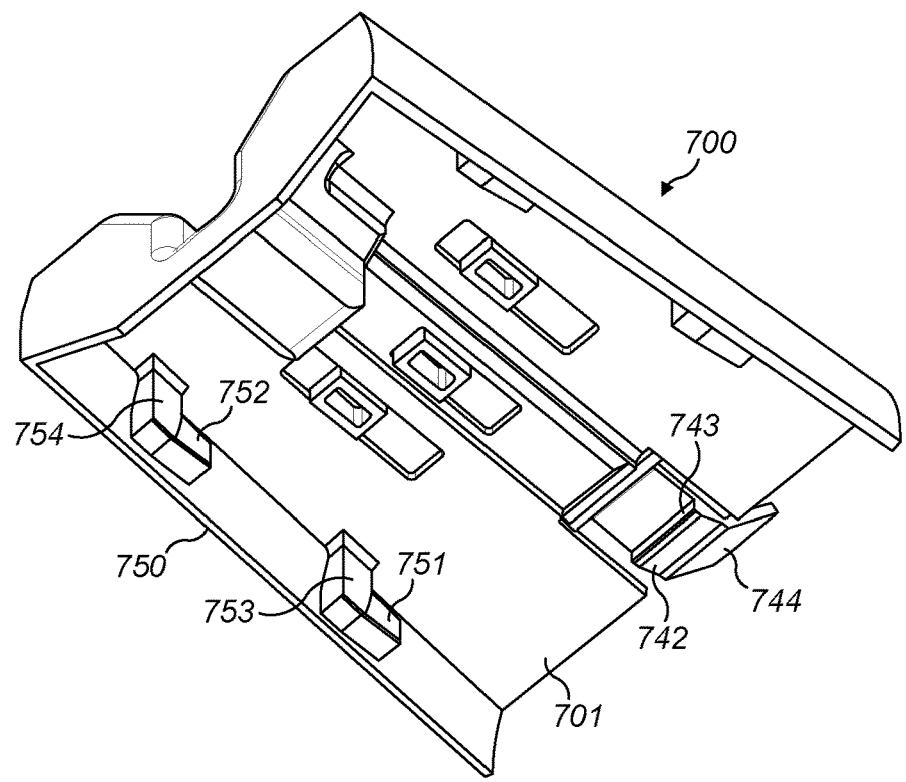

The sterile drape does not pass directly between the drive assembly interface 400 and the instrument interface 500. The drape comprises an interface structure 700 for interfacing between the drive assembly interface 400 and the instrument interface 500. FIGS. 7a and 7b show an exemplary interface structure 700 in isolation. The interface structure 700 is also shown in FIG. 6 attached to the drive assembly interface 400 and to the instrument interface 500. The interface structure 700 may be integrally formed with the drape. Alternatively, the interface structure 700 may be formed separately from the drape and subsequently attached to the drape. Either way, the interface structure 700 is sterile. One side 701 of the interface structure 700 directly contacts the drive assembly interface. The other side 702 of the interface structure 700 directly contacts the instrument interface. Thus, the interface structure 700 prevents the non-sterile drive assembly interface from directly touching the sterile instrument interface and hence maintains the sterile barrier between the two components.

The interface structure 700 comprises a main body 704 and drive transfer elements 706, 707, 708. The drive transfer elements are movable relative to the main body. The drive transfer elements are movable along linear paths. Conveniently, when the interface structure 700 is attached to the surgical robot arm, the main body 704 lies parallel to the surface(s) of the drive assembly interface 400. Suitably in this attached configuration, the main body 704 is aligned with the drive assembly interface.

As mentioned above, the interface structure 700 comprises drive transfer elements. In the example illustrated in FIGS. 7a and 7b, the interface structure comprises three drive transfer elements: a first drive transfer element 706, a second drive transfer element 707 and a third drive transfer element 708. The first drive transfer element 706 is slidably received in a first slot 726. The second drive transfer element 707 is slidably received in a second slot 727. The third drive transfer element 708 is slidably received in a third slot 728. Each drive transfer element is slidably movable along its respective slot.

A central portion 736 of the first drive transfer element 706 comprises a protrusion to the second side 702 of the interface structure 700. As can be seen from FIG. 7a, each of the drive transfer elements comprises a central portion which comprises a protrusion to the second side 702 of the interface structure 700. In this example, the central portions of the drive transfer elements comprise recesses to the first side 701 of the interface structure 700 (visible in FIG. 7b) for engagement with the fins of the respective drive assembly interface elements.

In other examples, the central portions of the drive transfer elements can be arranged the other way round. In other words, recesses can be provided towards the second side and protrusions can be provided towards the first side. Alternatively, any combination of protrusions and recesses can be provided. This can include one drive transfer element comprising either both a protrusion towards the first side and a protrusion towards the second side, or a recess towards the first side and a recess towards the second side. The configuration adopted will suitably match that of the drive assembly interface 400 and the instrument interface 500. In other words, where a drive assembly interface element comprises a protruding fin, the central portion of the respective drive transfer element towards the first side will comprise a recess for receiving the fin. Where the drive assembly interface element comprises a recess, the central portion of the respective drive transfer element towards the first side will comprise a protrusion for engaging with the recess. Similarly, where the instrument interface element comprises a protruding fin, the central portion of the respective drive transfer element towards the second side will comprise a recess for receiving the fin. Where the instrument interface element comprises a recess, the central portion of the respective drive transfer element towards the second side will comprise a protrusion for engaging with the recess.

Generally, each drive transfer element comprises a first portion and a second portion. The central portion suitably comprises the first portion and the second portion. The first portion is engageable with the robot arm. For example, the first portion is engageable with the drive assembly interface, such as being engageable with a drive assembly interface element. The second portion is engageable with the instrument. For example, the second portion is engageable with the instrument interface, such as being engageable with an instrument interface element.

To put it another way, at least one of the first portion and the second portion can be a drive transfer element recess, or a recess in the drive transfer element. At least one of the first portion and the second portion can be a drive transfer element protrusion, or a protruding portion of the drive transfer element. Preferably, the drive transfer element comprises both a drive transfer element recess and a drive transfer element protrusion.

The drive transfer element recess is engageable with an interface protrusion, such as a protrusion on a drive assembly interface element or on an instrument interface element. The drive transfer element protrusion is engageable with an interface recess, such as a recess in a drive assembly interface element or in an instrument interface element.

The interface structure comprises a first fastener 740 for retaining the interface structure 700 on the robot arm when the interface structure is mounted, or attached, to the robot arm. The drive assembly interface 400 comprises a retention lip 440. The first fastener 740 is engageable with the retention lip 440. The first fastener 740 comprises a ridge 742. During attachment of the interface structure 700 to the drive assembly 400, the ridge 742 passes over the retention lip 440. The first fastener is resilient to permit flexing so that the ridge 742 can pass over the retention lip 440. Once the first fastener has passed the retention lip, a flat portion 743 at the rear of the first fastener (in the direction of attachment) abuts a front portion of the retention lip (again, in the direction of attachment) and resists movement of the interface structure 700 in a direction away from the robot arm along the longitudinal axis 413 of the distal end 404 of the arm. In this way, the interface structure 700 is retained in position attached to the drive assembly interface 400. To remove the interface structure 700 from the robot arm, the first fastener can be released. The first fastener 740 is releasable by resiliently deforming the first fastener so as to lift the ridge 742 over the retention lip 440. In the example illustrated in FIGS. 7a and 7b, the first fastener comprises a tab 744. The tab 744 permits a user to lift the first fastener so as to disengage the ridge 742 from the retention lip 440. The tab 744 need not be provided in all examples. The engagement of the first fastener with the retention lip can provide tactile feedback that the interface structure is correctly or properly attached to the robot arm.

Additional retention features are provided on an edge 750 of the interface structure 700 in the illustrated example. As illustrated in FIG. 7b, one edge 750 of the interface structure comprises on an internal face thereof two lugs 751, 752. The lugs 751, 752 protrude inwardly from the internal face of the edge 750 of the interface structure 700. Cooperating retention features are provided on an outer edge of the drive assembly interface 400. Two passages 451, 452 are provided on the outer edge of the drive assembly interface 400 which communicate with a retention channel 453. In the illustrated example a common retention channel communicates with both passages, but this need not be the case. In alternatives, each passage can communicate with a respective retention channel. The passages 451, 452 and the retention channel 453 are formed as recesses in the outer edge of the drive assembly interface 400.

As the interface structure 700 is mounted to the drive assembly interface 400, the lugs 751, 752 will pass through the passages 451, 452 and into the retention channel 453. The interface structure 700 can be moved along the longitudinal axis 413 of the distal end of the arm 404. The retention channel 453 is parallel to the longitudinal axis 413 of the distal end of the arm. The movement of the interface structure in this direction (i.e. parallel to the longitudinal axis 413) moves the lugs along the retention channel 453 away from the openings to the passages 451, 452. At the same time, the first fastener 740 is moved to engage with the retention lip 440. When the lugs 751, 752 are moved away from the openings to the passages 451, 452, the interface structure will be restricted to move along the longitudinal axis 413 of the arm 404. The lugs 751, 752 will abut an upper edge 454 of the retention channel 453 to restrict movement of the interface structure 700 away from the drive assembly interface 400 in a direction transverse to the longitudinal axis 413. In other words, the engagement of the lugs in the retention channel will prevent or restrict the interface structure from being lifted off the drive assembly.

As can be seen from FIG. 7b, in this example the lugs 751, 752 comprise an upright portion 753, 754. As the interface structure is moved along the longitudinal axis 413 of the distal end of the arm 404 so as to engage the lugs in the retention channel 453, the front face of the upright portions 753, 754 will move into abutment with faces 455, 456 adjacent the passages 451, 452. This abutment between the upright portions 753, 754 and the faces 455, 456 serves to limit the movement of the interface structure, and provides tactile feedback that the limit of travel has been reached. The upright portions 753, 754 need not be provided in every example.

Thus this combination of retention features of the interface structure 700, i.e. the first fastener 740 and the lugs 751, 752, restricts the removal of the interface structure 700 from the robot arm.

In one example, prior to attaching the interface structure to the drive assembly interface, the drive assembly interface elements are driven to a desired position, such as an interfacing position. Suitably the interfacing position, or the desired position, is for engaging the drive assembly interface elements with respective drive transfer elements and/or respective instrument interface elements. This desired position is suitably with the drive assembly interface elements at one end of their respective travel, for instance towards the end of the drive assembly interface away from the proximal end of the robot arm. The interface structure can be arranged so that the drive transfer elements are correspondingly at cooperating positions within their respective travel, for instance with one of the drive transfer elements (suitably the drive transfer element with the shortest extent of travel) being at one end of its respective travel. In this way, the engagement of the drive transfer elements with the drive assembly interface elements is reliably effected. This method of engagement can be done without needing to drive or otherwise move the drive transfer elements and/or the drive assembly interface elements back and forth to effect engagement.

Engaging the interface structure with the drive assembly in this way can mean that the main body of the interface structure is then able to move relative to the drive assembly interface by up to the full travel of the drive transfer element with the shortest travel.

The surgical drape is packaged in a sterile package prior to being used. The drape can be packaged together with a packaging insert, examples of which are schematically shown in FIGS. 8 to 13. The packaging insert is packaged with the drape in a way so as to be engaged with the drape, for example by being engaged with the interface structure. The packaging insert provides a convenient way of holding and/or manipulating the drape in general, and the interface structure in particular, as the drape is engaged with the robot arm.

Once the drape has been engaged with the robot arm, the packaging insert can be removed from the drape. In the illustrated examples the packaging insert is disposable, and once removed from the drape it can be discarded. One method of using the packaging insert is as follows. The packaging insert is packaged together with the drape. When the drape packaging is opened, a user can hold the packaging insert and use it to position the interface structure of the drape onto the drive assembly interface of the robot arm. If appropriate, the packaging insert can be used to apply pressure to engage the interface structure with the drive assembly interface, for example by engaging one or more drive transfer elements with corresponding ones of drive assembly interface elements. The packaging insert could then be removed from the interface structure and discarded. The drive transfer elements which had been retained by the packaging insert, as will be described below, will then be free to move. The interface structure could then be moved along the drive assembly interface, for example towards a distal end of the arm, to cause engagement of the interface structure with the drive assembly interface. The remainder of the drape could then be applied to the robot arm, as discussed below.

Where the portion of the drape for positioning between the drive assembly interface and the instrument interface is a flexible and/or a compliant portion, the packaging insert can guide the flexible or compliant portion into engagement with the drive assembly interface. For example, where the drive assembly interface element comprises a cup or recess, the packaging insert can guide the flexible or compliant portion of the drape so as to sit within the cup or recess. The packaging insert can provide sufficient material of the drape so that adjacent drive assembly interface elements can move relative to one another without thereby tearing or ripping the material of the drape. The packaging insert suitably comprises a protruding portion around which the flexible or compliant portion sits, and which guides the flexible or compliant portion into the cup or recess.

The packaging insert 800 comprises a body 802 and an engagement portion 804 which is releasably engageable with the drape, for example by being releasably engageable with the interface structure. In the illustrated example the packaging insert comprises a second engagement portion 806. In other examples one or more engagement portion can be provided. The provision of the engagement portion is not necessary in all examples. The engagement portion can cause a portion of the drape, for example the interface structure, to remain fast with the packaging insert when engaged thereto. The engagement between the packaging insert and the drape permits the drape to be manipulated by manipulation of the packaging insert. Suitably the engagement portion is engaged with the drape when the drape is in its sterile package. Thus, on opening the sterile package, a user can hold the packaging insert and can straightforwardly use it to position the drape on the robot arm.

Figure 8:
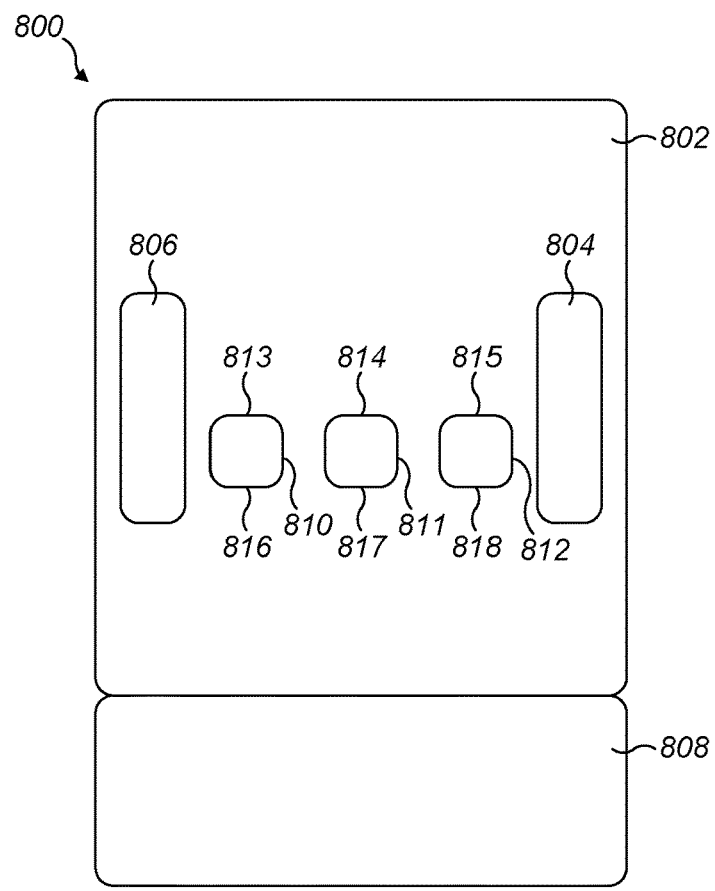
FIG. 8 illustrates a schematic plan view of a packaging insert.

Suitably the packaging insert 800 comprises a handle 808 for permitting a user to more easily hold and/or manipulate the packaging insert. In the example illustrated in FIG. 8, the handle 808 is in the form of a tab. The tab is provided adjacent the body 802. Suitably the handle may comprise a raised portion, permitting a user to hold the packaging insert without needing to touch the drape itself. This can assist in retaining the sterility of the drape as it is positioned on the robot arm. The handle can take any suitable form on and/or adjacent the body of the packaging insert. Referring to FIG. 8, the handle is provided along one side of the body 802 of the packaging insert 800. In other examples, the handle can be provided along less than the whole length of one side, for example to one end or another, or centrally. In other examples more than one handle can be provided. For example, two handles can be provided along one side of the body 802, or at least one handle can be provided along two or more sides of the body 802. The handle or handles can be unitary with the body of the packaging insert. This configuration can facilitate ease of manufacture.

Suitably the packaging insert can be held and manipulated by a user using only one hand. The handle can be configured and/or sized to be holdable by a single hand. A user may therefore be able to use the packaging insert to position the drape with one hand, and may use the other hand to manipulate the remainder of the drape. In this way, a single user can correctly position the drape over the drive assembly interface, and can also position the remainder of the drape over the end of the robot arm.

The engagement of the engagement portion with the drape is releasable. Once the drape is positioned as desired on the robot arm, the packaging insert is removed from the drape. This can be achieved by the engagement of the packaging insert with the drape being weaker than the engagement of the drape with the robot arm, as will be discussed in more detail below.

The engagement portion can comprise an adhesive portion 804. The adhesive portion can, prior to or as part of the packaging of the drape, be adhered to the drape. Suitably the adhesive portion is adhered to the interface structure 700. The adhesive portion is of sufficient strength to hold the drape and permit manipulation of the drape by the packaging insert. Once the drape is mounted to the robot arm, for example by the interface structure being engaged with the drive assembly interface (such as by the drive transfer elements being engaged with the drive assembly interface elements) or being retained on the drive assembly by the fastener 740 and/or the lugs 751, 752, pulling on the packaging insert 800 away from the drive assembly interface 400 will cause the engagement portion to disengage from the drape. In other words, the adhesive portion holds the drape with a force which is weaker than that with which the interface structure engages with the drive assembly interface or with which the fastener 740 and/or the lugs 751, 752 retain the interface structure 700 on the drive assembly.

Suitably the packaging insert 800 comprises a plurality of engagement portions. The packaging insert can comprise a plurality of adhesive portions. The adhesive portions 804, 806 can be provided on opposite sides of the packaging insert 800. This configuration permits a more stable engagement between the packaging insert and the drape. In the example illustrated in FIG. 8, the packaging insert comprises two adhesive portions. A first adhesive portion 804 is provided towards a first edge of the packaging insert 800. A second adhesive portion 806 is provided towards a second edge of the packaging insert 800. In other examples, different numbers of adhesive portions can be provided.

The packaging insert 800 comprises a plurality of apertures 810, 811, 812. The apertures are configured to receive therethrough a portion of a respective drive transfer element, for example part of the central portion of a drive transfer element. In the example illustrated in FIG. 8 three apertures are provided, corresponding to the three drive transfer elements illustrated in FIG. 7a. A protruding portion, such as a fin, of a first drive transfer element 706 is receivable through a first aperture 810. A protruding portion, such as a fin, of a second drive transfer element 707 is receivable through a second aperture 811. A protruding portion, such as a fin, of a third drive transfer element is receivable through a third aperture 812.

The apertures comprise respective retention portions. Referring to FIG. 8, the retention portion comprises a forward edge (the uppermost edge of the aperture in the orientation of FIG. 8) of each of the apertures. The first aperture 810 comprises a first forward edge 813. The second aperture 811 comprises a second forward edge 814. The third aperture 812 comprises a third forward edge 815.

The retention portions retain the drive transfer elements. For instance, the retention portions retain the drive transfer elements in the desired position for interfacing with the drive assembly interface elements. Where the drive transfer element is retained at one end of its respective travel, the packaging insert need only comprise one retention portion for each aperture and/or for each drive transfer element. In other words, the respective drive transfer element need only be retained behind the respective forward edge of the aperture. The drive transfer element can, in this configuration, be restricted from moving away from the retention portion by virtue of it being at an end of its respective travel. The retention portion restricts the drive transfer element from moving forwards (i.e. in an upwards direction in the orientation of FIG. 8), and ensures that as the interface structure is placed into position on the drive assembly interface, the drive transfer elements align with the drive assembly interface elements.

Where the desired (or interfacing) position of a drive transfer element is not at an end of its travel, the aperture of the packaging insert usefully comprises a rear edge opposing the forward edge. The rear edge is spaced from the forward edge by the length (along the direction of motion) of the drive transfer element, for example the protruding portion or fin, that is receivable through the aperture. The drive transfer element is retained between the forward edge and the rear edge. The first aperture 810 comprises a first rear edge 816. The second aperture 811 comprises a second rear edge 817. The third aperture 812 comprises a third rear edge 818. Each aperture 810, 811, 812 is sized to retain the drive transfer element via an interference fit. Thus, where the drive transfer elements are retained by apertures of the packaging insert in an interference fit, the apertures can act as the engagement portion.

In the example illustrated in FIG. 8, the three apertures 810, 811, 812 are arranged in a line across the body of the packaging insert. That is to say, the apertures are aligned with one another. This need not be the case. In other examples the interfacing positions of the drive transfer elements need not be aligned, thus the apertures therefore also need not be aligned. The apertures can be provided in any suitable location across the body of the packaging insert.

In other examples, a greater or fewer number of apertures can be provided. In the example illustrated in FIG. 9, a single aperture 901 is provided. Each of the drive transfer elements is receivable through this common aperture 901. This configuration can be used where each of the drive transfer elements is aligned in the interfacing position. The retention portion in this example comprises a forward edge 903 of the single aperture 901.

In other examples, any suitable number of apertures can be provided. Suitably each drive transfer element is receivable through one of one or more apertures provided in the packaging insert.

In one example of the instrument interface, three drive transfer elements are provided. The outer two drive transfer elements have a range of motion of, for example, 10.2 mm. The central drive transfer element has a range of motion of, for example, 6 mm. Thus, suitably the central drive transfer element is retained by the packaging insert at one end of its range of motion, so that the interface structure can be moved along the drive assembly interface by up to 6 mm during attachment. The outer two drive transfer elements are suitably retained by the packaging insert so that they are able to move by up to 6 mm as well. If attachment of the interface structure to the drive assembly interface is effected by a shorter travel than 6 mm, then the drive transfer elements can accordingly be retained in configurations that permit this shorter travel once the interface structure has been mounted onto the drive assembly interface.

The packaging insert has been discussed above as comprising one or more apertures to receive therethrough a protruding portion of a corresponding drive transfer element. Where the drive transfer element comprises a recess instead of a protrusion, the packaging insert can comprise a protruding portion to engage with the recess. The packaging insert can comprise apertures and/or protrusions to correspond with the configuration of the interface structure. In other words, where the drive transfer element comprises a protrusion to the second side 702 (i.e. the side of the interface structure 700 to which the packaging insert is engaged), the packaging insert can comprise a corresponding recess or aperture. Where the drive transfer element comprises a recess to the second side 702, the packaging insert can comprise a corresponding protrusion. Suitably, where the packaging insert comprises a protrusion, the retention portion comprises a forward edge of the protrusion. Similarly to the above discussion, this permits the drive transfer element to be retained in position, i.e. in the desired or interfacing position, by the packaging insert.

The adhesive portions 804, 806 illustrated in FIG. 8 are provided on the body 802 of the packaging insert 800. In another example illustrated in FIG. 9, the packaging insert 900 comprises two side folds 912, 914 provided on opposite sides of the body 902. A first side fold 912 comprises two adhesive portions 904, 906. A second side fold comprises a further two adhesive portions 908, 910. The provision of the adhesive portions on side folds of the packaging insert permits the adhesive portions to adhere to the sides of the interface structure rather than to the main body of the interface structure. This permits a stable engagement between the packaging insert and the interface structure. This configuration also permits the adhesive portions to be disengaged from the drape whilst the body of the packaging insert retains the interface structure in position. Once disengaged, the packaging insert can be removed quickly and/or easily without disturbing the position of the interface structure. This can therefore help to ensure that the interface structure remains in the correct position as the packaging insert is removed.

In one example, the body 802, 902 can itself be adhesive. For example the whole of the body can be adhesive.

The adhesive force, or attractive force, can be provided by a 'smooth-on-smooth' contact. For example at least a portion of the body of the packaging insert facing the interface structure can be smooth, and at least a portion of the interface structure facing the packaging insert can be smooth. The smooth portions are suitably arranged to face one another so that they come into contact when the packaging insert is attached to the interface structure. The close proximity of these smooth surfaces can provide sufficient adhesive force to retain the packaging insert on the interface structure.

Figure 9:
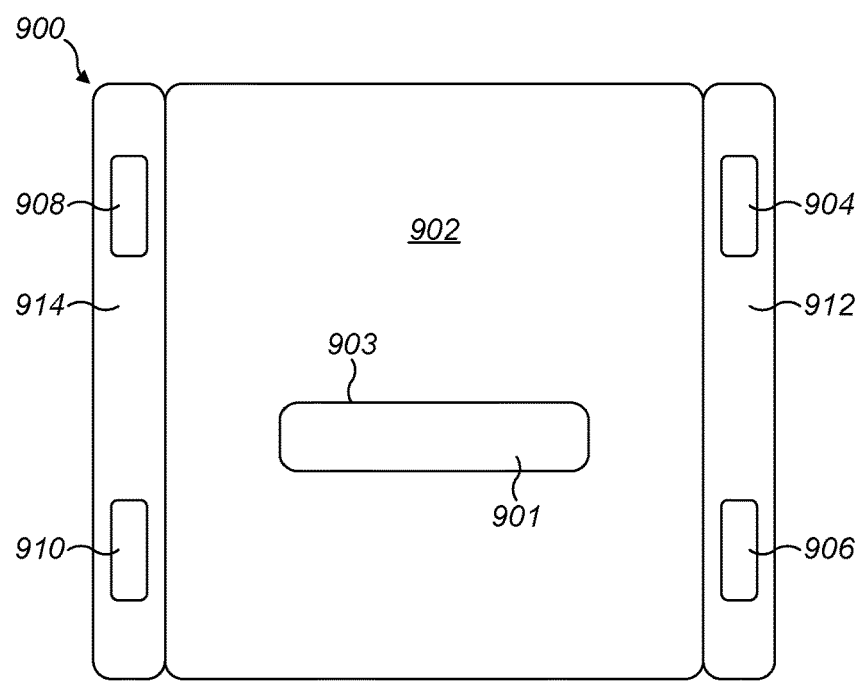
FIG. 9 illustrates a schematic plan view of another packaging insert.

In the example illustrated in FIG. 9, the side folds 912, 914 are provided along the length of the body 902. This need not be the case. In other examples, a side fold can be shorter than the length of the body of the packaging insert. The side folds need not be of equal length. One side fold can be shorter than the other side fold. For example, the first side fold can extend along the length of the body and comprise two adhesive portions. The second side fold can extend adjacent a shorter central part of the body and comprise a single adhesive portion. In this way, three adhesive portions are provided which can engage with the interface structure in a stable manner. Other combinations of length of side fold, numbers of adhesive portions on each side fold, and positioning of the adhesive portions on the side folds are also possible.

Figure 10A:
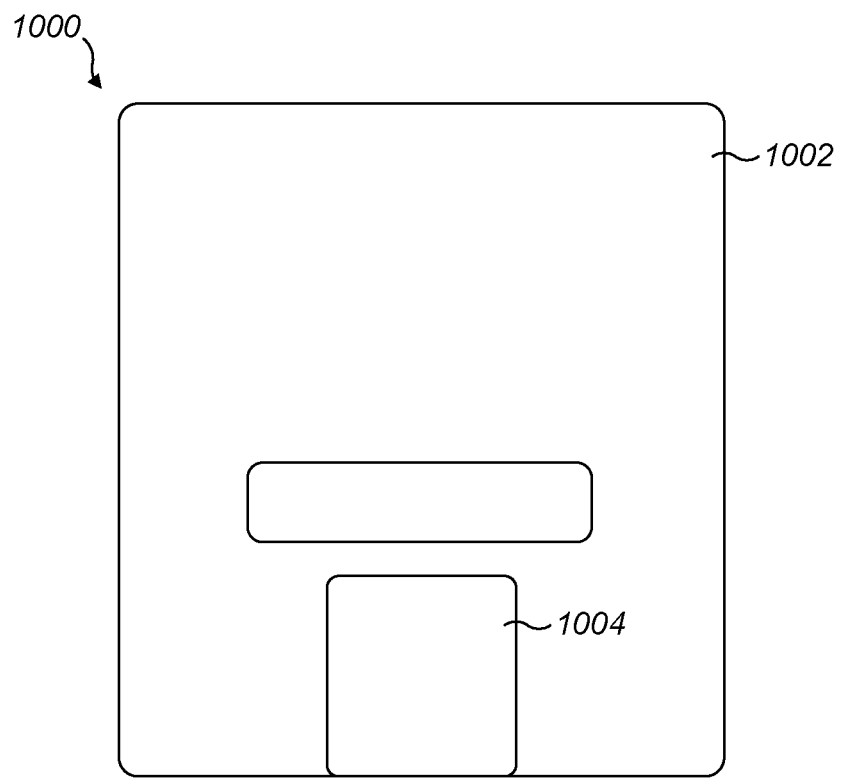
FIG. 10a illustrates a schematic plan view of another packaging insert.
Figure 10B:
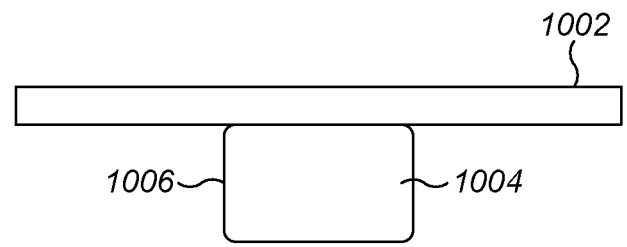

Referring now to FIGS. 10*a* and 10*b*, in one example the engagement portion comprises a protrusion 1004 which protrudes from an underside of the body 1002 of the packaging insert 1000. The protrusion 1004 is sized and shaped to engage via an interference fit with an indent 712 in the interface structure. The protrusion 1004 is suitably deformable to as to fit within the indent 712 and yet stiff enough to be able to frictionally engage therewith, for example with walls of the indent 712, so as to hold the packaging insert 1000 together with the interface structure 700.

Figure 11A:
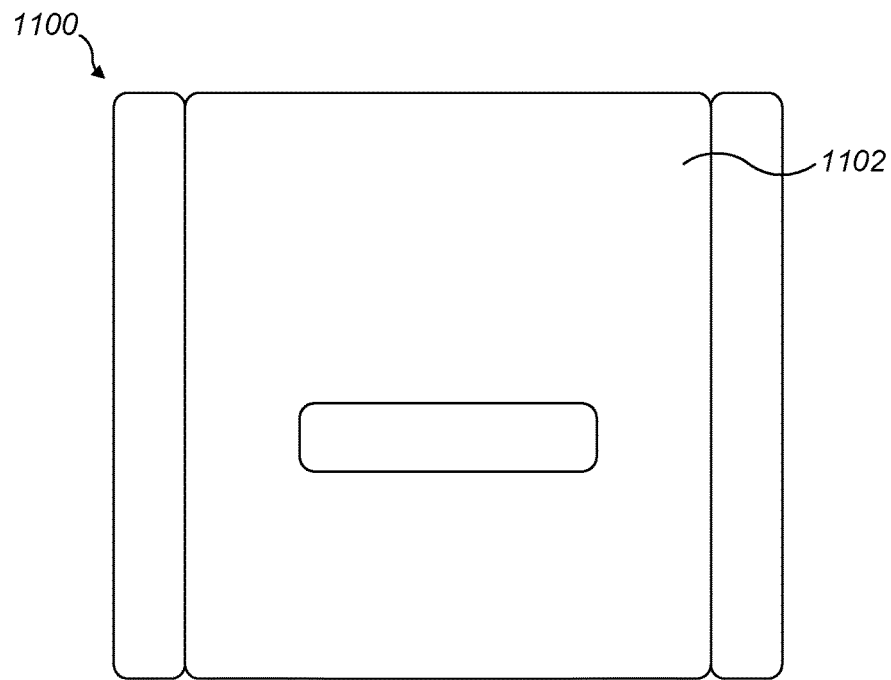
FIG. 11a illustrates a schematic plan view of another packaging insert.
Figure 11B:
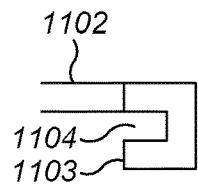

In another example, illustrated in FIGS. 11a and 11b, the engagement portion of the packaging insert 1100 comprises a lip 1103. The lip 1103 is provided on a side fold adjacent the body 1102 of the packaging insert 1100. The lip could instead be provided on the body 1102 of the packaging insert 1100. As illustrated, the lip 1103 faces inwardly (i.e. towards a central portion of the packaging insert 1100. The inwardly facing lip 1103 is configured to engage with a corresponding outwardly facing lip or L-shaped projection provided on the interface structure (not shown). A portion of the outwardly facing lip on the interface structure is receivable into a recess 1104 adjacent the inwardly facing lip 1103. Suitably a pair of opposing lips 1103, 1105 are provided on the packaging insert, which are engageable with a corresponding pair of opposing lips provided on the interface structure.

The lip 1103 is suitably resilient and/or deformable. The lip 1103 can engage with the interface structure lip by a push attachment, which can cause the lip 1103 to pass over the interface structure lip and thereby to engage with it to hold the packaging insert together with the interface structure. The lip can comprise a chamfered portion, or lead-in, on its lower edge to assist in engaging the packaging insert with the interface structure in a push fit.

The packaging insert can be disengaged from the interface structure by disengaging the lip 1103 from the interface structure lip. As mentioned above, the lip 1103 can be resilient and/or deformable. The force needed to resiliently deform the lip 1103 so as to disengage the packaging insert from the interface structure is preferably less than the force with which the interface structure is retained on the drive assembly interface, for example by the fastener 740 and/or the lugs 751, 752.

Figure 11C:
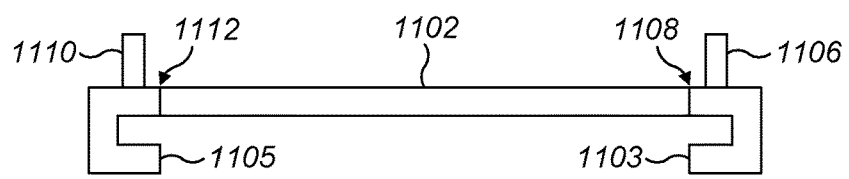
FIG. 11c illustrates a schematic side view of a packaging insert.

Referring to FIG. 11c, the packaging insert 1100 comprises a tab 1106 coupled to the lip 1103. The tab 1106 is provided on an upper side of the packaging insert. The packaging insert comprises a pivot portion 1108, about which the lip 1103 can pivot relative to a remainder of the packaging insert. The pivot portion 1108 can be a crease or fold, or other weakened portion of the packaging insert. The packaging insert is configured so that as the lip 1103 pivots about the pivot portion 1108, the lip 1103 disengages with the lip of the interface structure. The tab is provided to one side of the pivot portion 1108 so that pressing sideways on the tab 1106 causes the lip 1103 to pivot about the pivot portion 1108. In this way, the lip 1103 can be disengaged from the interface structure lip via movement of the tab 1106.

Suitably a second tab 1110 is provided adjacent a second lip 1105, to one side of a second pivot portion 1112. Movement of the second tab 1110 likewise causes the second lip 1105 to pivot about the second pivot portion 1112. This disengages the second lip 1105 from a corresponding interface structure lip.

Suitably the tabs 1106, 1110 are provided so that moving the distal ends of the tabs towards one another causes disengagement of the lips 1103, 1105 from the interface structure. In other words, a pinching motion can be used by a user to disengage the packaging insert 1100 from the interface structure 700. This pinching motion can be done with a single hand. The tabs 1106, 1110 and pivot portions 1108, 1112 are examples of a deformable portion which can deform so as to move the lip 1103 from a position in which it is engaged with a corresponding lip of the interface structure to a position in which it is disengaged from the corresponding lip of the interface structure.

The lips or flanges 1103, 1105 on the packaging insert 1100 need not be inwardly facing. In other examples the lips 1103, 1105 on the packaging insert 1100 can be outwardly facing lips which are engageable with inwardly facing lips on the interface structure.

Figure 12:
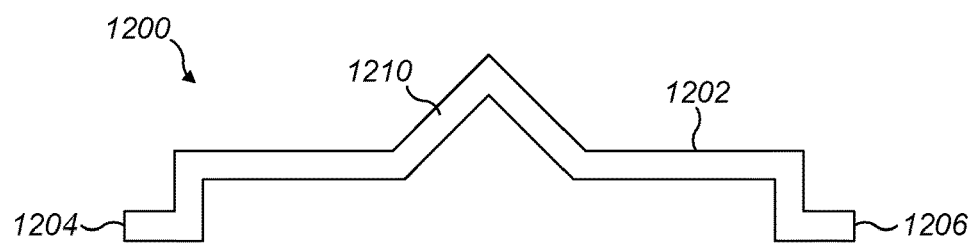
FIG. 12 illustrates a schematic side view of another packaging insert.
Figure 13:
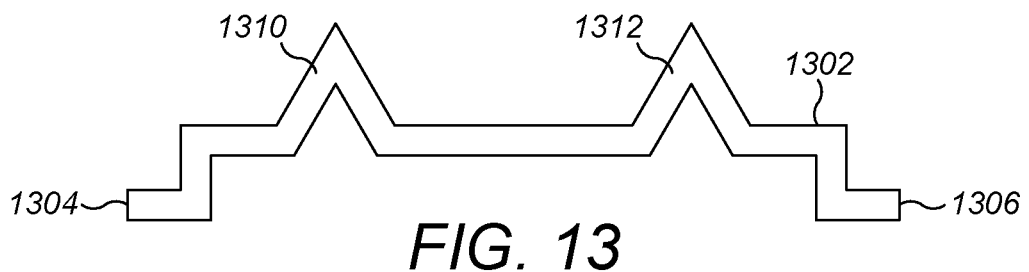
FIG. 13 illustrates a schematic side view of another packaging insert.

Examples of such configurations are illustrated in FIGS. 12 and 13. The packaging insert 1200 illustrated in FIG. 12 comprises two outwardly facing lips 1204, 1206. The packaging insert 1300 illustrated in FIG. 13 comprises two outwardly facing lips 1304, 1306.

FIGS. 12 and 13 also show examples of alternative deformable portions. A deformable portion can take the form of a single fold (as in FIG. 12, at 1210) or multiple folds such as two folds (as in FIG. 13, at 1310, 1312). The folds preferably extend from the top side of the packaging insert to permit ease of holding by a user.

The fold or folds are configured so that on pinching the fold, the lowermost portions of the fold are brought together. This causes the outwardly facing lips 1204, 1206, 1304, 1306 to move from an engaged position in which they are engageable with corresponding lips of the interface structure to a disengaged position in which they are disengaged from the corresponding lips of the interface structure. Thus, pinching the fold or folds can disengage the packaging insert 1200, 1300 from the interface structure.

In the example illustrated in FIG. 11, the lips 1103, 1105 extend along the whole length of the side of the body 1102 of the packaging insert 1100. Similarly, the lips 1204, 1304 can extend along the whole length of the side of the body 1202, 1302 of the packaging insert 1200, 1300 shown in FIGS. 12 and 13. Preferably the lips 1204, 1304 do not extend along the whole length of the side of the body. This can mean that the deformable portion, i.e. the fold or folds, need not extend along the whole length of the side of the body. This can permit other engagement portions, such as one or more adhesive portions, to be provided on the body for engagement with the drape. It also permits the retention portion to be provided in a more convenient manner on the body.

The provision of lips and folds as described above advantageously permits formation of the packaging insert from a sheet of material by a stamping and/or bending process. This allows the formation of the packaging insert by a cost-effective method. The packaging insert is suitably made from a resilient and/or deformable material. Preferably the packaging insert is made from a sheet material. Suitably the packaging insert is made from cardboard. Making the packaging insert from cardboard permits it to be easily folded and/or cut into the desired shape, and enables it to be formed in a low-cost manner, which conveniently permits the packaging insert to be a disposable part. The packaging insert can be disposed of together with standard surgical waste, for example by incineration.

The engagement portion can be provided in any combination of the above-mentioned examples of engagement portion. Any one or more of any type of engagement portion can be provided with any one or more of any other type of engagement portion. Similarly, the retention portion can be provided in any combination of the above-mentioned examples of retention portion. Any one or more of any type of retention portion can be provided with any one or more of any other type of retention portion.

Suitably the packaging insert comprises an indication of orientation. This can prevent the drape being incorrectly positioned on the robot arm. For example, the packaging insert can comprise a feature indicating a particular orientation with respect to the robot arm and/or the drive assembly interface. Preferably the packaging insert comprises an orientation feature which permits the drape to be positioned on the robot arm in the correct orientation and restricts the drape from being positioned on the robot arm in an incorrect orientation.

Suitably the orientation feature comprises one or more of the aperture 901 or apertures 810, 811, 812, the side folds 912, 914, the protrusion 1004 and the handle 808.

Examples have been discussed above that comprise only one or some of the features of the packaging insert. Likewise, the illustrated examples comprise a subset of the features of the packaging insert. This is for ease of understanding. It will be understood that any feature can be combined with any other feature as desired.

A surgical drape assembly can comprise a drape and the packaging insert as described above packaged together with the drape. As discussed above, the packaging insert is configured to be held with one hand. Thus with one hand a user can position the drape, such as the interface structure of the drape, on the drive assembly of the robot arm. With another hand, a user can place the remainder of the drape, such as the flexible material of the drape, over a remaining portion of the robot arm.

Figure 14:
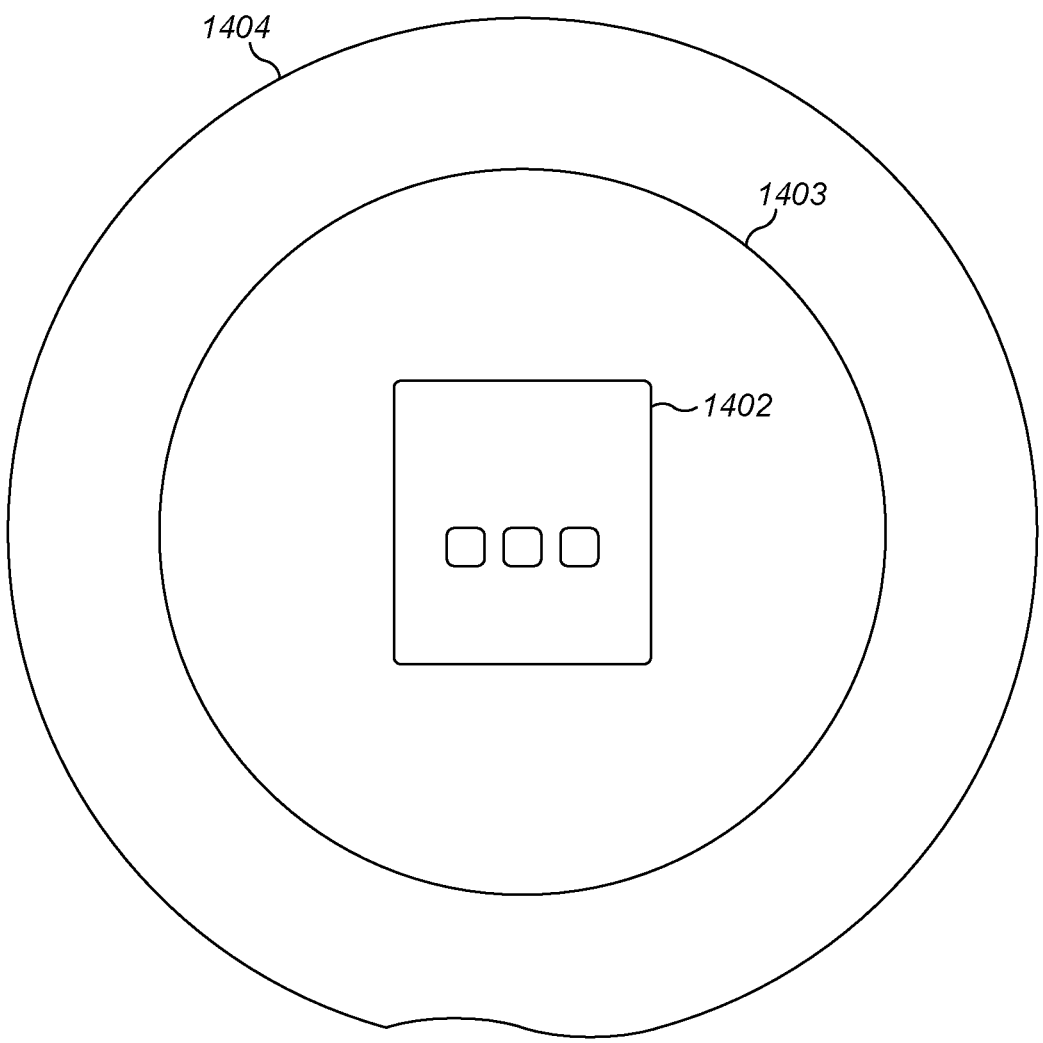
FIG. 14 illustrates a schematic plan view of a packaging insert packaged with a drape.

Suitably the drape comprises one or more reinforcement portions. The reinforcement portion can comprise a strengthened or stiffened portion of the drape. Suitably the reinforcement portion comprises a ring or part-ring, such as a horseshoe shape. The reinforcement portion permits a user, with one hand, to hold the reinforcement portion and use it to place the drape over the robot arm. An example of a packaged drape assembly comprising reinforcement portions is illustrated in FIG. 14. The illustrated drape assembly comprises a body 1402 of a packaging insert engaged with a portion of the drape. The drape comprises two reinforcement portions. An inner reinforcement portion comprises a ring 1403. Conveniently the inner reinforcement portion 1403 is flexible. An outer reinforcement portion comprises a part-ring 1404. The outer reinforcement portion 1404 is suitably flexible. The outer reinforcement portion can deform to permit ease of location of the drape over the robot arm. The resilience in the outer reinforcement portion 1404 also provides an engagement with the robot arm. For example, the outer reinforcement portion 1404 can act as a clip for holding the drape on the robot arm.

Additionally or alternatively, the drape can comprise attachment features, for example one or more fastener, such as clips or magnetic attachments, which clip or attach to the robot arm. The attachment features are preferably configured to attach to particular features of the robot arm. Suitably, the fasteners fasten to complimentary fasteners, such as complimentary-shaped fasteners, on the robot arm. For example, the fastener on the reinforcement portion may be a clip which fastens to a complimentary-shaped recess in the surface of the robot arm. The fasteners may take any suitable form, for example clips, clasps, buckles, latches, plugs, sockets, hooks, eyes, poppers, eyelets, buttons, and/or hook and loop fasteners such as Velcro as long as they are capable of securing the reinforcement portion to the arm whilst the arm is being manipulated.

The drape suitably comprises a series of attachment features which are configured to pass at least one of along and around the robot arm. In other words, the drape can comprise a series of attachment features which are configured to attach to a series of successive points on the robot arm between the distal end of the robot arm and the base. Additionally or alternatively, the drape can comprise a series of attachment features which are configured to attach to a series of points around the circumference of the robot arm, for example adjacent a joint of the robot arm.

In this way, the drape can be conveniently located on the robot arm. Each time a drape is applied to the robot arm (suitably this will be a new drape each time, since each drape is suitably disposable) the drape can be repeatably located on the robot arm. This consistency of location of the drape on the robot arm can help to ensure that there is sufficient freedom of movement permitted to ensure that the robot arm is unhindered in its desired movements.

In some examples the drape comprises a first portion and a second portion. The drape can comprise a first reinforcement portion at an end of the first portion and a second reinforcement portion at an end of the second portion. The first reinforcement portion and the second reinforcement portion are suitably configured to be engageable with one another in a sealing manner so as to permit the first portion of the drape and the second portion of the drape to be joined to one another so as to maintain the sterile barrier. For example, the first portion may be generally conical, for covering the distal portion of the robot arm. The second portion may be generally cylindrical for covering a more proximal portion of the robot arm.

In some examples, the reinforcement portions are hollow. Suitably the reinforcement portions comprise at least a portion of a cooling structure for cooling the robot arm. The hollow portion of the reinforcement portion is suitably in communication with a source of cooling fluid. The cooling fluid might be air, or any other suitable fluid. Conveniently, the use of air as a cooling fluid means that the cooling fluid can safely be emitted to the surroundings of the robot arm.

The reinforcement portion suitably has a series of orifices. These orifices are openings in the outer surface of the reinforcement portion which go through to the hollow portion. In other words, they are through-holes. Cooling fluid inside the reinforcement portion passes through these orifices to the exterior of the reinforcement portion. Thus, the orifices are bleed holes for the cooling fluid. The orifices are directional. They enable the cooling fluid to be aimed in particular directions. Suitably, the orifices are directed towards the robot arm in order to feed cooling fluid from the reinforcement portion towards the robot arm.

The orifices may be regularly spaced around the surface of the reinforcement portion facing the robot arm. Alternatively, the orifices may be arranged around the surface of the reinforcement portion facing the robot arm so as to only be located on those parts of the reinforcement portion which are directed to the portion of the robot arm which is to be cooled.

The reinforcement portion suitably comprises biasing projections. Each biasing projection is directed towards the robot arm, and is configured to contact the robot arm so as to space the reinforcement portion from the robot arm. The biasing projections thus support the reinforcement portion. They prevent the reinforcement portion from directly contacting the robot arm. They thus prevent the reinforcement portion from hindering movement of the robot arm. Suitably, there are at least two biasing projections per reinforcement portion. There may be more than two biasing projections per reinforcement portion. Each biasing projection may take any suitable form, for example a leaf spring. The biasing projection can comprise an attachment feature, such as a fastener.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical drape assembly comprising:
    a surgical drape comprising:
        a drive transfer element for transferring drive between a surgical robot arm and a surgical instrument;
    a packaging insert configured to engage a portion of the surgical drape for locating the surgical drape on the surgical robot arm, the packaging insert being releasably engageable with the surgical drape and comprising:
        a body; and
        a retention portion engageable with the drive transfer element for retaining the drive transfer element in a desired position.

2. The surgical drape assembly as claimed in claim 1, the surgical drape comprising reinforcement portions.

3. The surgical drape assembly as claimed in claim 1, in which the packaging insert comprises an engagement portion releasably engageable with the surgical drape.

4. The surgical drape assembly as claimed in claim 3, in which the engagement portion is provided on an underside of the body.

5. The surgical drape assembly as claimed in claim 4, in which the engagement portion comprises at least one lip engageable with a respective drape lip provided on the surgical drape.

6. The surgical drape assembly as claimed in claim 5, in which the packaging insert comprises a deformable portion configured to deform so as to move the at least one lip from a position in which the at least one lip is engaged with the respective drape lip to a position in which the at least one lip is disengaged from the respective drape lip.

7. The surgical drape assembly as claimed in claim 5, in which the packaging insert comprises a deformable portion corresponding to the at least one, the deformable portion being configured to deform so as to move the at least one lip from a position in which the at least one lip is engaged with the respective drape lip to a position in which the at least one lip is disengaged from the respective drape lip.

8. The surgical drape assembly as claimed in claim 4, in which the engagement portion comprises a protrusion configured to protrude into a corresponding recess on the surgical drape, the protrusion being sized to engage with the recess in an interference fit so as to frictionally engage therewith.

9. The surgical drape assembly as claimed in claim 3, in which the engagement portion comprises an adhesive portion which is releasably adherable to the surgical drape.

10. The surgical drape assembly as claimed in claim 3, in which the packaging insert comprises at least one side portion to a respective side of the body, a respective engagement portion being provided on each of the at least one side portion.

11. The surgical drape assembly A packaging insert as claimed in claim 3, in which the engagement portion is configured to engage with the surgical drape with a weaker engagement than an engagement between the surgical drape and the robot arm such that the drape is preferentially retained on the robot arm.

12. The surgical drape assembly as claimed in claim 1, in which the retention portion comprises at least one of a recess, an aperture and a protruding portion.

13. The surgical drape assembly as claimed in claim 1, in which the retention portion comprises an aperture in the body, the aperture comprising a first edge, and the first edge being configured to retain the drive transfer element in the desired position.

14. The surgical drape assembly as claimed in claim 13, in which the aperture comprises a second edge opposing the first edge, the first edge and the second edge being spaced apart so as to be frictionally engageable with opposing sides of the drive transfer element.

15. The surgical drape assembly as claimed in claim 13, in which the surgical drape comprises three drive transfer elements, and the packaging insert comprises three apertures in the body, each aperture being configured to receive a respective one of the drive transfer elements therethrough and comprising a respective edge configured to retain the respective drive transfer element in the desired position.

16. The surgical drape assembly as claimed in claim 1, in which the packaging insert comprises a handle.

17. The surgical drape assembly as claimed in claim 1, in which the packaging insert is formed from a single piece of material by at least one of stamping and bending.

18. The surgical drape assembly as claimed in claim 1, in which the packaging insert comprises a rigid and/or a semi-rigid material.

19. The surgical drape assembly as claimed in claim 1, in which the packaging insert is configured to be packaged together with the surgical drape.

* * * * *